United States Patent [19]

Hall, II

[11] Patent Number: 4,557,419
[45] Date of Patent: Dec. 10, 1985

[54] TEMPERATURE-ACTUATED FLOW CONTROL DEVICE

[75] Inventor: George R. Hall, II, Wickliffe, Ohio

[73] Assignee: The Babcock & Wilcox Company, New Orleans, La.

[21] Appl. No.: 467,554

[22] Filed: Feb. 17, 1983

[51] Int. Cl.[4] ........................................... G05D 23/02
[52] U.S. Cl. .............................. 236/93 R; 236/101 E; 417/187
[58] Field of Search ......... 417/187; 236/93 R, 101 E, 236/101 R, 87, 48; 137/843, 517; 251/75

[56] References Cited

U.S. PATENT DOCUMENTS

| | | | |
|---|---|---|---|
| 3,930,613 | 1/1976 | Place | 236/87 X |
| 3,970,106 | 7/1976 | Harris | 137/843 |
| 4,141,379 | 2/1979 | Manske | 137/843 |
| 4,441,356 | 4/1984 | Bohl | 236/93 R X |

Primary Examiner—William E. Wayner
Attorney, Agent, or Firm—Vytas R. Matas; Robert J. Edwards

[57] ABSTRACT

A temperature-actuated flow control device has a fluid inlet connected to an exhaust line with a control chamber located therebetween. The control chamber has a free-floating bi-metallic circular element which is flexed in response to temperature changes between a first position stopping flow between the inlet and the exhaust line and a second position opening the flow therebetween. This flow control device, when adapted to a gas sampling system, allows the bi-metallic element remain in a first position at normal operating temperatures to permit the continuous sampling of the sample gas. Whenever the temperature falls below the dew point of the sample gas, the bi-metallic element returns to its second position to stop the sampling of sample gas by the system to prevent condensation in the system.

4 Claims, 4 Drawing Figures

SECTION A-A

TEMPERATURE-ACTUATED FLOW CONTROL DEVICE

TECHNICAL FIELD

This invention relates to flow control devices in general and in particular to a new and useful gas flow control device for gas analyzing apparatus utilizing a bi-metal switch to control gas flow in the apparatus.

BACKGROUND ART

The present invention has application to the control of all fluids which require a reduction of fluid flow or a shut-off fluid flow due to critical temperature changes in the fluid. The invention has particular application in the construction of gas analyzers which use heated sampling systems to prevent liquid condensation in the system and which systems draw a gas through the system by using an aspirator to affect the gas flow. It is desirable in such devices to interrupt the aspiration of gas flow when the gas sample temperature falls below the dew point causing condensation within the apparatus. Known devices use a temperature sensor and a solenoid valve to control the aspirating air stream by shutting it on and off. Such an arrangement involves expensive electrical circuitry and connections as well as piping which frequently limits its applicability due to ambient effects on the valve and electrical components.

SUMMARY OF THE INVENTION

In accordance with the present invention, the flow of an aspirating gas and, hence, the flow of a control gas is regulated by use of a snap-acting bi-metallic switch which is mounted in a chamber of an aspirator inlet passage to thereby control the flow of the aspirated gas easily and automatically. The bi-metallic switch is a disc or similar element which has an area which overlies and closes the aspirator air passage whenever the temperature of operation is not in a satisfactory range. The bi-metal element is chosen to achieve the desired control in the predetermined temperature range and is located in the aspirated chamber where it is not appreciably affected by the aspirating air. The bi-metal element provides excellent control within the desired temperature range of the sample. The bi-metal switch is made free-floating in a chamber having a height and diameter larger than the switch. The chamber surface having the controlled opening is tapered to make the switch self-aligning with the opening thus insuring positive closure and repeatability. Thus, a simple bi-metallic device will accomplish the same function as an electrical control valve but in a less expensive and easily-installed manner.

Accordingly, it is an object of the present invention to provide an improved temperature actuator fluid control in which a sample gas flow is regulated by the flow of an aspirating gas and this aspirating gas flow is controlled by a bi-metallic element which closes off the flow whenever a desired gas temperature is not achieved.

Yet another object of the present invention is to provide a gas sampling device which includes a free-floating bi-metallic switch mounted in a tapered area having a switch-controlled opening to make the switch self-centering with respect to the opening.

Still another object of the present invention is to provide a temperature-actuated fluid flow control for a gas sampling device having a free-floating bi-metallic switch which has symmetrical gas flow around the switch to insure repeatable switch action.

These and other objects of novelty which characterize the present invention are pointed out with particularity in the claims annexed to and forming a part of this disclosure. For a better understanding of the present invention, its operating advantages and specific objects attained by its uses, reference is made to the accompanying drawings and descriptive matter in which a preferred embodiment of the invention is illustrated.

DETAILED DESCRIPTION OF THE PREFERRED EMBODIMENT

Figure 1:
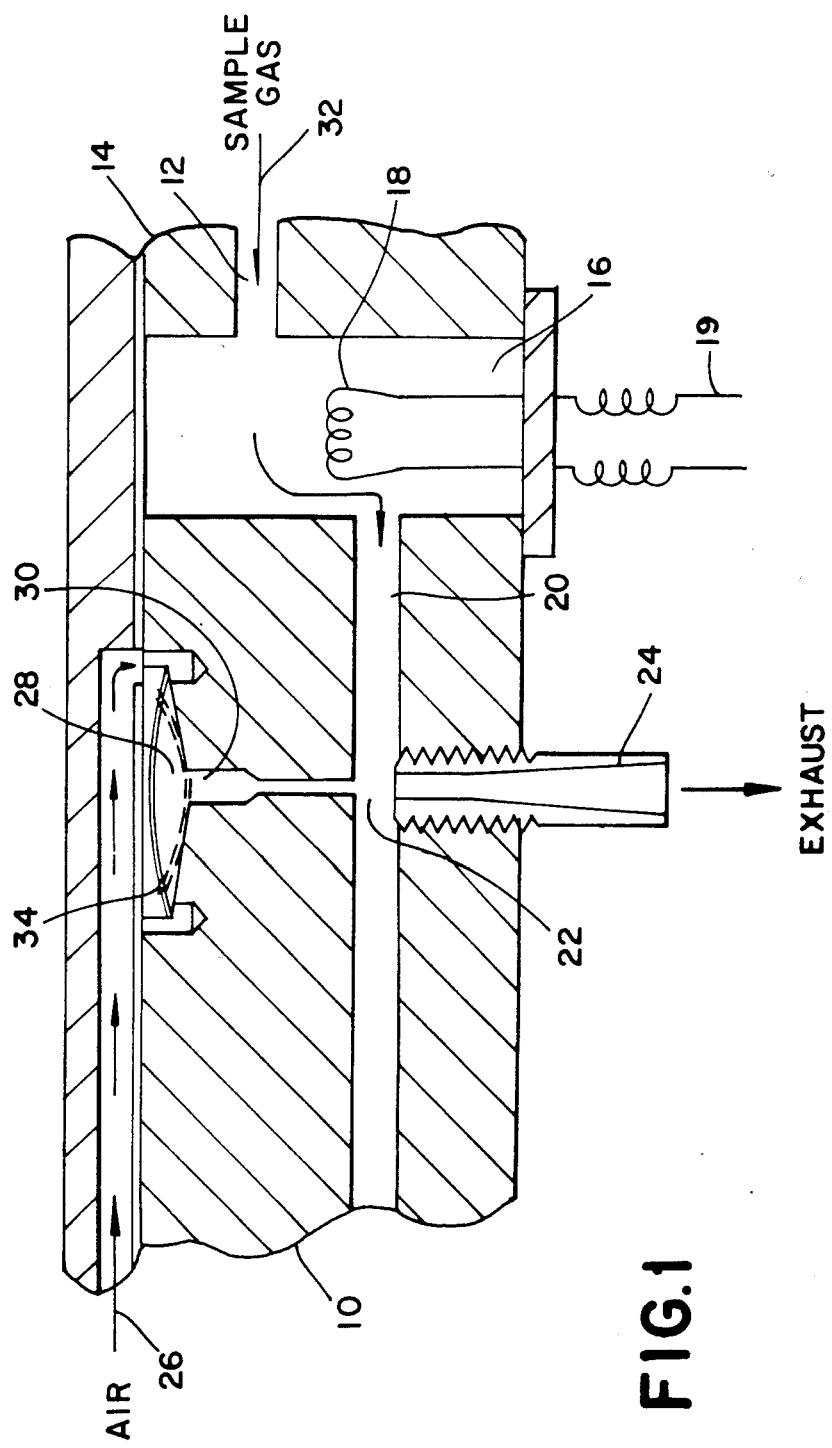
FIG. 1 is a partial sectional view of a gas sampling device constructed in accordance with the present invention.
Figure 2:
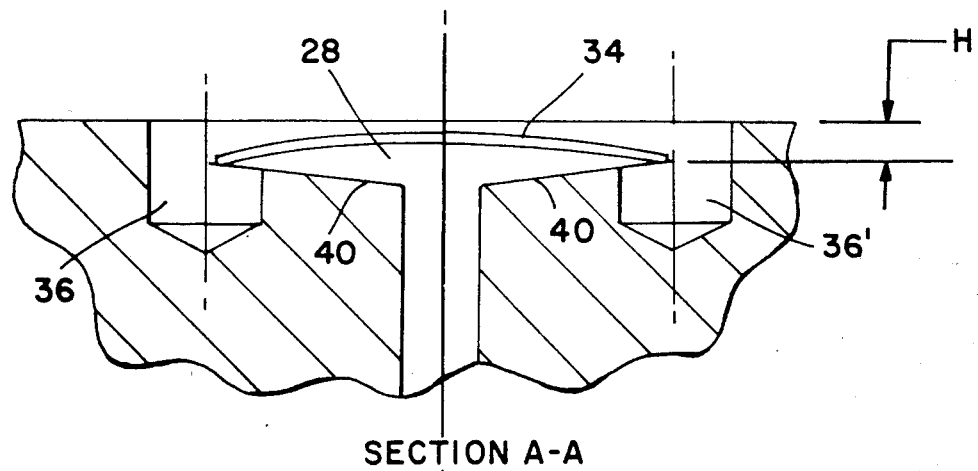
FIG. 2 is an expanded view of a bi-metallic element in the open flow position and the mounting area for same of the device of FIG. 1.
Figure 3:
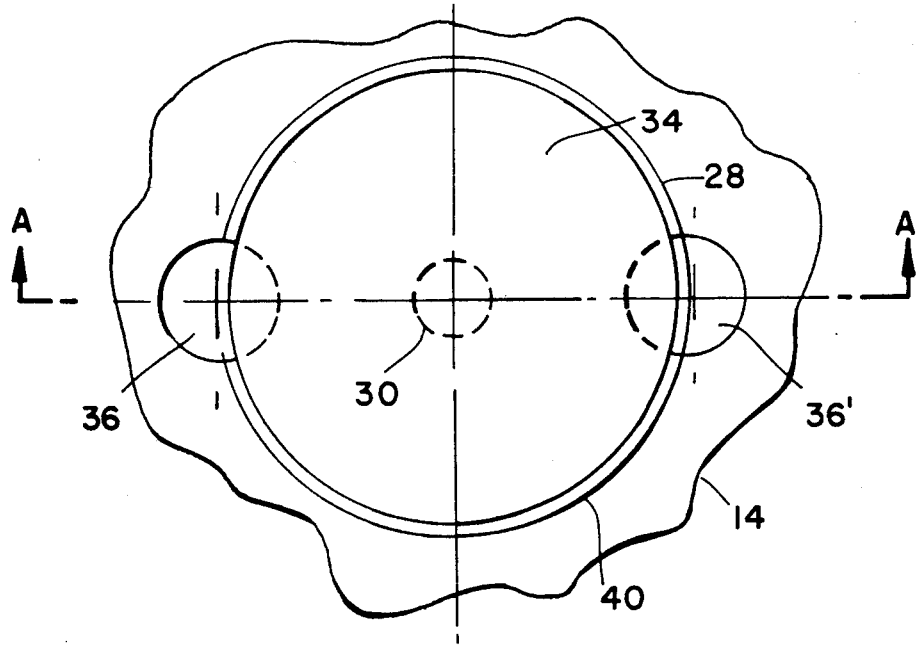
FIG. 3 is a top view of the bi-metallic switch and mounting area of FIG. 2.

Referring to the drawings wherein the showings are for purposes of detailing a preferred embodiment of the invention but not limiting the invention thereto, FIGS. 1 through 3 show a temperature-actuated fluid flow control device generally designated 10 which in the embodiment illustrated comprises a device for sampling a gas. The device 10 includes an inlet passage 12 for the inflow of a gas sample into a heated block or housing 14 which contains a separate sampling chamber 16 having a gas sensing device 18 which may, for example, include means for determining the type of gas and possibly the quantity of such gas in a particular sample flow. As shown, the gas sensor 18 is connected through electrical lines 20 to suitable instruments for determining the desired gas sample characteristics. The sample gas then flows through a reduced flow area section 20 followed by an aspirating chamber 22 and then out through an exhaust or discharge area 24. The flow of the sample gas through the inlet 12 is controlled by the flow of an aspirating gas which is admitted in the direction of an arrow 26 into an aspirating gas flow control chamber 28 through an opening 30 into the chamber 22 and then out the exhaust 24. This flow induces the flow of the sample gas through the inlet 12.

The flow of the sample gas in the direction of arrow 32 is controlled by the flow of the aspirated gas in the direction of the arrow 26 through the opening 30. A bi-metallic element 34 is disposed in the aspirating chamber 28 and it may be flexed from the solid line indicated position to the dotted line indicated position in accordance with predetermined temperature changes of the aspirating gas. The bi-metallic element is made up of metals having characteristics which will permit it to operate in the desired temperature range and it is advantageously in the form of a disc as may be best seen in FIGS. 2 and 3. The construction may be of any shape such that it will close the opening 30 when the temperature is other than a correct operating temperature.

In the embodiment of the invention shown as a gas analyzer when the block 14 is at proper operating temperature the bi-metallic element 34 will remain in the solid line position and permit flow of aspirating gas and inflow of the sample gas in the direction of the arrow 32 by allowing air around its periphery to exit into the passage 30. If the block temperature cools below the desired temperature, the bi-metallic element abruptly changes to the dotted line position thereby blocking air flow to the passage 30 and the aspirator to thereby shut off the sampling process. In so doing, it eliminates the possibility of condensate forming in the sample gas passageways. The bi-metallic element 34 is fabricated by bonding two metals together which have different thermal coefficients of expansion. By proper selection of metals and diameters and sizes, etc., the element is made to deflect abruptly in order to rapidly cause displacement or exert forces.

Figure 4:
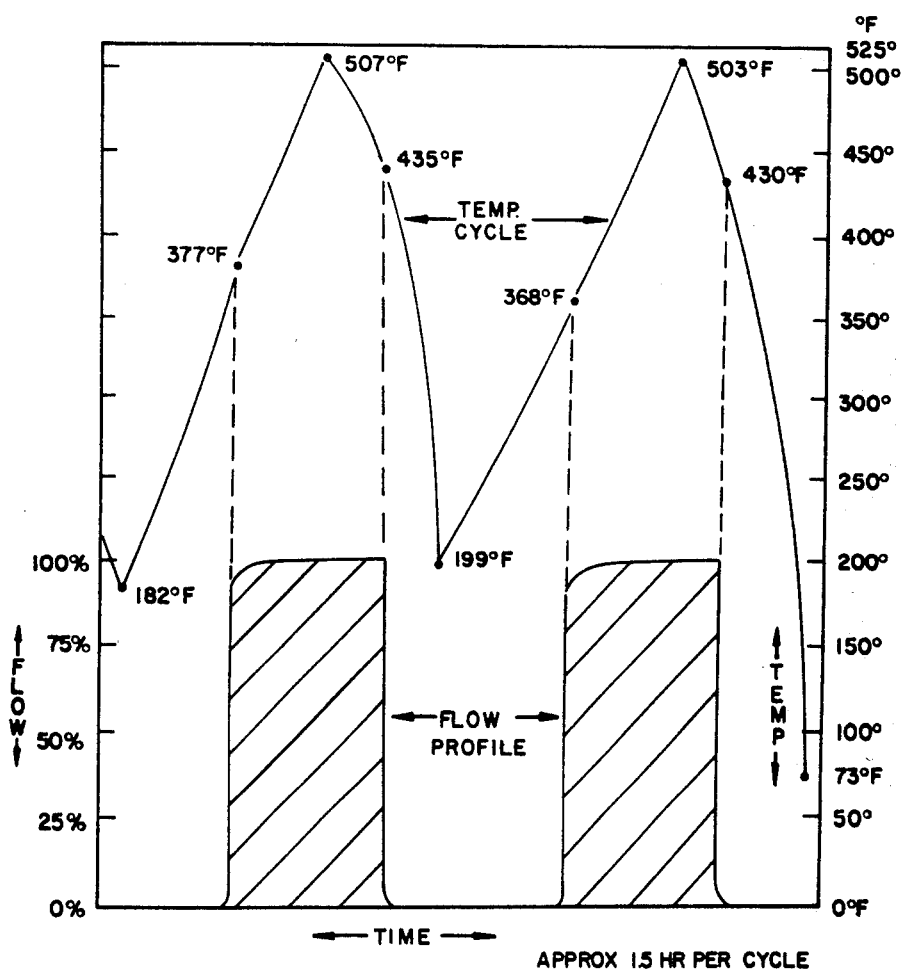
FIG. 4 is a graphical representation of the operation of the device of FIG. 1 in response to temperature change.

As may be better seen with particular reference to FIGS. 2 through 4, the bi-metallic element 34 is made to be free-floating within the control chamber 28. Free-floating in the present embodiment is indicated to have a clearance of approximately 0.010 inches along the radius of the chamber 28 when the bi-metallic element 34 is of a diameter approximately 0.625 inches in its FIG. 2 position. The height clearance is approximately 0.008 inches on the chamber height H of 0.032 inches. This ability of the bi-metallic element 34 to float within the chamber 28 prevents it from being jammed in undesired positions as well as provides an adequate leakage of air from the inlet 26 to the passage 30. To make the bi-metallic element 34 self-centering with respect to the passage 30, a tapered section 40 is formed at the bottom of the chamber 28 which may be best described as a tapered section 40 having the passage 30 at its center and angled towards the passage 30. The taper is approximately 0.004 inches and this taper is sufficient to make the free-floating bi-metallic element 34 self-centering with respect to the passage 30.

As may be best seen with particular reference to FIGS. 2 and 3, the tapered section 40 is formed between centers of a pair of counterbored sections 36 and 36' located along a diameter of the tapered section 40 and the center of passage 30. The counterbores 36 and 36' are approximately 0.156 inches in diameter and are approximately 0.125 inches deep. The purpose of these counterbores is to provide unrestricted flow resulting in a swift and large volume of air flowing from the inlet 28 to both sides of the bi-metallic element 34, thus making it speedily responsive to temperature changes by maintaining a substantial volume of the same air on both sides of the bi-metallic element 34.

The bi-metallic element 34 is manufactured to specification as is known by those skilled in the art to have a movement of approximately 0.02 inches between a snap temperature at static flow of approximately 380° F. and a reset temperature of approximately 330° F.

As may be best described with particular reference to FIG. 4, which describes an actual snapping operation of the bi-metallic element with time over a series of temperature cycles lasting approximately 1.5 hrs./cycle. From the curve, it may be seen that flow from port 28 to the passage 30 remains at approximately 0 percent over a time interval until the temperature in passage 28 reaches approximately 377° F., at which time the bi-metallic element 34 snaps to its FIG. 1 solid line position allowing 100 percent of the flow from the passage 28 to the passage 30. Raising the temperature to 507° F. and then dropping it back down causes the bi-metallic element 34 to snap to its dotted line position as indicated in FIG. 1 at a temperature of 435° F. Further decrease in the temperature to 199° F. and then raising it back up maintains the bi-metallic element 34 in its dotted line FIG. 1 position sealing approximately all of the flow between the passages 28 and 30 until the temperature reaches 368° F. at which time the bi-metallic element 34 snaps to its solid line FIG. 1 position allowing 100 percent of the flow between passages 28 and 30. The raising of the temperature to 503° F. and then dropping it back down causes the next switch to occur at 430° F. It may thus be seen that with the foregoing construction, the bi-metallic element 34 provides a positive closure and opening of the passage 30 at repeatable temperatures.

Certain modifications and improvements will occur to those skilled in the art upon reading the foregoing description. It will be understood that all such improvements and modifications have been deleted herein for the sake of conciseness and readability but are properly within the scope of the following claims.

I claim:

1. A temperature-actuated fluid flow control device comprising:
    a fluid inlet;
    an exhaust line for the fluid connected to said fluid inlet;
    means for inducing flow of fluid into said fluid inlet and out said exhaust line;
    a switching chamber located between said fluid inlet and said exhaust line;
    a bi-metallic flexible element disposed in said switching chamber and being flexibly responsive to temperature change to move between a first flexed position wherein the element stops the flow of fluid between said fluid inlet and said exhaust line and a second flexed position opening flow between said fluid inlet and said exhaust line; and
    said switching chamber being larger than said bi-metallic element to make said bi-metallic element free-floating in said switching chamber and having a centrally located outlet port communicating with said fluid outlet from a tapered area substantially covered by said flexible element and inclined toward said outlet port to make said bi-metallic element self-centering with said outlet port during closure to insure the positive and repeatable closure thereof.

2. A temperature-actuated fluid flow control device as set forth in claim 1 wherein said bi-metallic element has a predetermined height and where the height of said switching chamber is greater than the height of said bi-metallic element.

3. A temperature-actuated fluid flow control device as set forth in claim 2 wherein said bi-metallic element is circular and wherein said switching chamber is also circular but having a radius larger than the radius of said bi-metallic element.

4. A temperature-actuated fluid flow control device as set forth in claim 3 wherein said switching chamber has a pair of counterbored areas formed at the extreme ends of a diameter of said switching chamber to allow the symmetrical flow of fluid past said bi-metallic element.

* * * * *

UNITED STATES PATENT AND TRADEMARK OFFICE
CERTIFICATE OF CORRECTION

PATENT NO. : 4,557,419
DATED : Dec. 10, 1985
INVENTOR(S) : George R. Hall, II

It is certified that error appears in the above–identified patent and that said Letters Patent are hereby corrected as shown below:

Column 2, line 40 change "20" to --19--.

Signed and Sealed this

Twenty-seventh Day of January, 1987

Attest:

DONALD J. QUIGG

*Attesting Officer*  *Commissioner of Patents and Trademarks*